(12) United States Patent
Buchholz et al.

(10) Patent No.: US 6,683,164 B1
(45) Date of Patent: Jan. 27, 2004

(54) RECOVERY OF ISOQUERCETIN FROM BIOFLAVANOID PASTES

(75) Inventors: Herwig Buchholz, Frankfurt (DE); Michael Jungnitz, Frankfurt (DE); Michael Grund, Darmstadt (DE); Ralf Rosskopf, Munster (DE); Hartmut Härtner, Muhltal (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/009,485

(22) PCT Filed: Jun. 6, 2000

(86) PCT No.: PCT/EP00/05182

§ 371 (c)(1),
(2), (4) Date: May 10, 2002

(87) PCT Pub. No.: WO00/76992

PCT Pub. Date: Dec. 21, 2000

(30) Foreign Application Priority Data

Jun. 16, 1999 (DE) .......................................... 199 27 425

(51) Int. Cl.[7] .......................... C07G 3/00; C07H 15/00; C07H 17/00

(52) U.S. Cl. ........................................... 536/18.5; 536/8
(58) Field of Search ..................................... 536/8, 18.5

(56) References Cited

U.S. PATENT DOCUMENTS 6,420,142 B1 * 7/2002 Buchholz et al.

FOREIGN PATENT DOCUMENTS

WO  WO 00 26399 A  5/2000

OTHER PUBLICATIONS

Chemical Abstracts, vol. 67, No. 17, Oct. 23, 1967, Abstract No. 82035k, p. 7729.

* cited by examiner

Primary Examiner—James O. Wilson
Assistant Examiner—Traviss C. McIntosh, III
(74) Attorney, Agent, or Firm—Millen, White, Zelano & Branigan, P.C.

(57) ABSTRACT

The invention relates to a method for recovering high-purity isoquerectin from bioflavonoid pastes, that is from mother-liquor residues which are produced during the recovery of flavonoids, by extraction with a solvent mixture of methyl acetate and water.

12 Claims, 1 Drawing Sheet

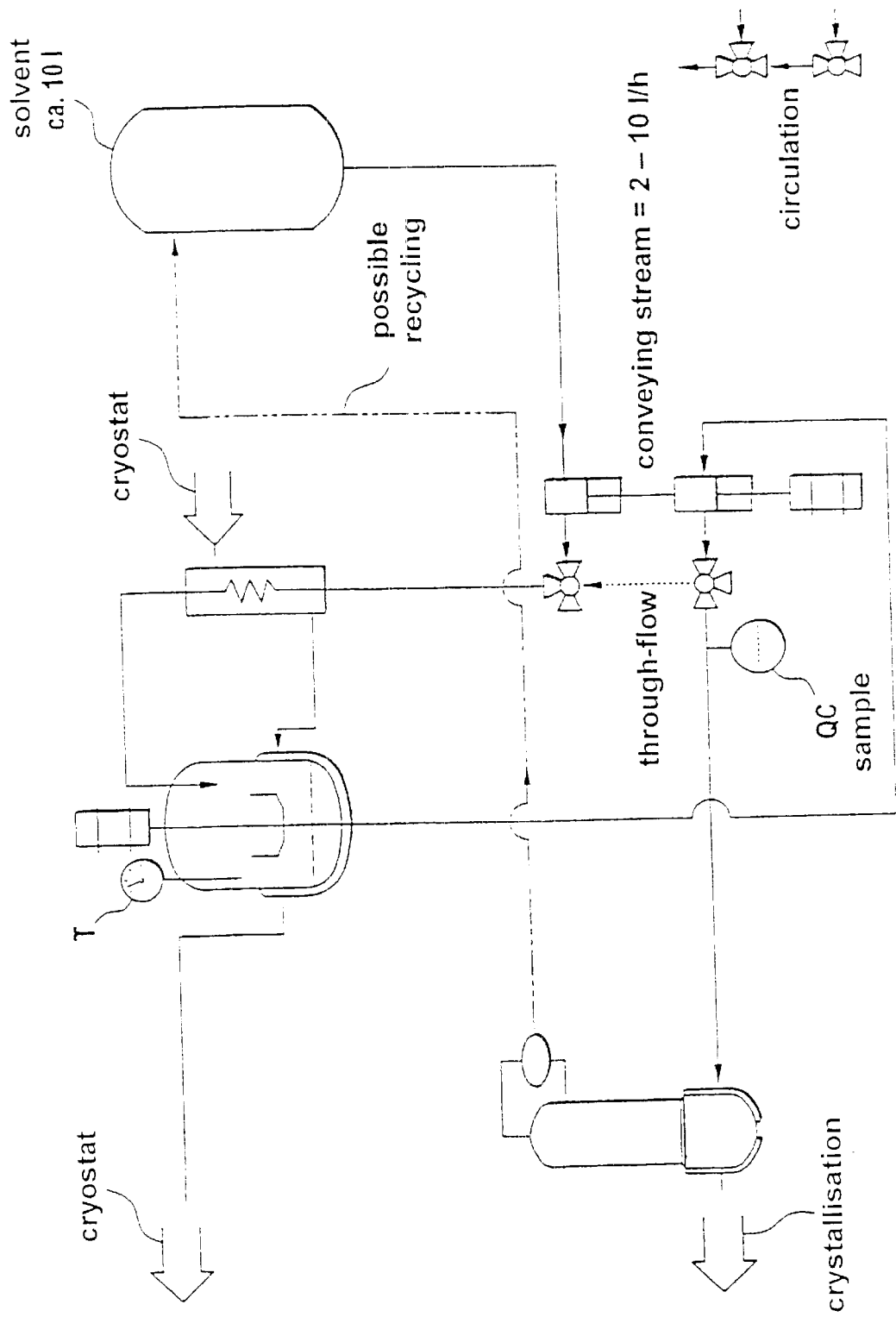

RECOVERY OF ISOQUERCETIN FROM BIOFLAVANOID PASTES

The present invention relates to a process for the recovery of high-purity isoquercetin from bioflavanoid mother-liquor residues by extraction of these residues with a solvent mixture comprising methyl acetate and water.

Isoquercetin and also other flavanoids, such as, for example, rutin, have recently been researched intensively owing to their special properties as antioxidants. Free radicals and reactive oxygen compounds play a major role in the human body in respect of ageing and the occurrence of illnesses.

Antioxidants, such as the flavanoids or also vitamin C, are able to scavenge such free radicals and substances and thus reduce their effect on the organism.

Flavanoids, in particular isoquercetin, which also play a major role in combination with vitamin C, are therefore nowadays frequently used and administered as food supplements in pharmaceutical formulations.

The demand for high-purity flavanoids, such as quercetin, rutin or in particular isoquercetin, is therefore increasing. The processes should be inexpensive, and the high-purity products should be obtained in as few reaction steps as possible.

The object was therefore to find an effective process for the recovery of high-purity isoquercetin from the cheapest possible starting material, where the purity of the isoquercetin should preferably be greater than 90% (HPLC).

Surprisingly, it has now been found that high-purity isoquercetin can be recovered from bioflavanoid pastes by extraction of these residues with a solvent mixture comprising methyl acetate and water.

The invention therefore relates to a process for the recovery of isoquercetin from bioflavanoid pastes (mother-liquor residues formed, for example, in the preparation of rutin from Dimorphandra gardneriana), which is characterised in that the following steps are carried out:

a) extraction of the mother-liquor residues (pastes) with a solvent mixture comprising methyl acetate and water in the volume ratio 9:1 in a ten-fold excess, based on the weight of the mother-liquor residues employed, at an extraction temperature of from 35° to 50° C., and with an extraction time of at least 30 minutes, and separation from the solid raffinate by centrifugation, b) dilution of the extract with water, c) removal of the methyl acetate from the extract by distillation under atmospheric pressure, d) rapid cooling of the aqueous distillation residue to 10° C, during which the isoquercetin starts to precipitate, e) immediate separation and drying of the product.

The bioflavanoid pastes are mother-liquor residues which remain behind in the preparation of pure flavanoids and which usually also contain other flavanoids in relatively large amounts. These residues represent a favourable starting material for the recovery of other flavanoids.

For example, Dimorphandra gardneriana (fava d'anta), contains isoquercetin as a second flavanoid besides rutin, and this inevitably then also arises in the mother liquor during the preparation of rutin. The extraction of mother-liquor residues (pastes) of this type for the recovery of isoquercetin is the subject-matter of this invention.

The isoquercetin is extracted from the mother-liquor residues ('pasta seca') with a solvent mixture comprising methyl acetate and water in the volume ratio 9:1 in a ten-fold excess, based on the weight of the mother-liquor residues employed, i.e. 10 l of extractant per kg of pasta seca, and separated from the solid raffinate by centrifugation. The raffinate, replenished with fresh pasta seca, can be employed for further extractions.

The raw material here is preferably pre-sieved and introduced slowly into the reactor.

Preference is given to the use of acid-free methyl acetate in order that possible hydrolysis of the isoquercetin is suppressed. The solvent mixture is therefore buffered, for example using a buffer such as ammonium hydrogencarbonate.

The extraction temperature is from 35° to 50° C. and is thus significantly below the boiling point of methyl acetate (from 55° to 57° C.). At higher temperature, losses in yield, losses of extractant and filtration difficulties must be expected.

The extraction time is at least 30 minutes. The extraction is preferably carried out for from 30 to 60 minutes. Although a longer extraction time of up to 6 hours does not cause any damage, it only improves the purity to an insignificant extent.

The extract is diluted with water (demineralised water), preferably 60–80% by volume, particularly preferably 60–70% by volume, of the amount of extract, and the methyl acetate is distilled off under atmospheric pressure. A bottom temperature of at most 70° C. is preferably selected here.

The extract should wherever possible be further processed immediately within 1 hour, since otherwise reductions in purity due to uncontrolled crystallisation may occur.

The addition of the amount of water may optionally also be carried out in portions and delayed until during the distillation.

The distillate still contains about 5% by weight of water (by the Karl Fischer method) and can be re-used after adjustment of the water content. About 85% by weight of the methyl acetate employed can be recovered in this way.

The aqueous distillation residue is cooled rapidly to 10° C., preferably within a maximum of 2 hours, during which the isoquercetin begins to precipitate.

About 80% of the total amount of isoquercetin precipitating precipitates in very finely crystalline form with high purity directly during the cooling. An HPLC check shows that the product consists of 94% of isoquercetin, 1% of rutin and 0.2% of quercetin. The preferred aim of recovering isoquercetin in a purity of greater than 90% is thus achieved.

The product must be separated off immediately, since on further stirring the crystal structure becomes coarser and the content drops since essentially only quercetin precipitates.

The product is then dried, which is preferably carried out in a vacuum drying cabinet at from about 80 to 120 mbar and a drying temperature of at most 45° C.

Should it be impossible to process the extract further immediately or should the precipitated product have stood for too long by mistake, a reduction in purity can be expected. However, the purity of the desired isoquercetin can be further improved by further purification steps.

A possible further purification step that may be mentioned is, for example, removal of quercetin impurities by stirring with methyl tert-butyl ether.

Another possibility for further purification is brief boiling with water followed by filtration.

For performance on a larger scale, the process according to the invention can also be carried out semi-continuously. The semi-continuous process is also a subject-matter of this invention.

The procedure here is to pass the requisite amount of solvent (where the solvent mixture is likewise composed of methyl acetate and water in the volume ratio 9:1) through an extractor with filter plate which contains a highly concentrated suspension of mother-liquor residues.

The extractor volume and volume flow rates are set in such a way that a residence time in the extractor of at least 30 minutes is maintained. After a run-in phase from one residence time during which the extractor is operated in circulation, fresh, temperature-controlled solvent mixture is passed into the extractor and at the same time the same amount of extract is withdrawn, so that the working volume in the extractor remains constant. The temperature in the extractor here is selected between 35° and 50° C.

The withdrawn extract is immediately concentrated to give the aqueous residue, it being possible for the distillate (water content 4.2%) to be reused directly for the extraction after water adjustment.

If the further steps of crystallisation, where appropriate also the purification by boiling with water and stirring with methyl tert-butyl ether are carried out in the same apparatus after discharge of the extraction residue, the continuously solid product phase remains in the apparatus for the entire time, and consequently some filtration steps are superfluous, thus minimising product and operating-material losses.

During purification of the crude isoquercetin, purification by boiling with water may also be preferred to removal of quercetin using MTBE'ether, since it may also be possible to remove some of the quercetin with the aqueous mother liquor.

FIG. 1 shows by way of example a diagram of a semi-continuous plant of this type.

However, the process according to the invention in the batch method when carried out in correspondingly large extraction vessels, for example enamel apparatuses, is likewise highly suitable for the isolation of large amounts of isoquercetin in a very pure state without further purification steps.

With the process described here, a method has been made available for obtaining high-purity isoquercetin extremely economically in relatively large amounts.

Even without further comments, it is assumed that a person skilled in the art will be able to utilise the above description in the broadest scope. The preferred embodiments are therefore merely to be regarded as descriptive disclosure which is absolutely not to be understood as limiting in any way.

The complete disclosure content of all applications and publications mentioned above and below is incorporated into this application by way of reference.

The following examples will explain the invention in greater detail.

EXAMPLE 1

0.625 kg of ammonium hydrogencarbonate are dissolved completely in 5 l of demineralised water in a suspension vessel. 45 kg of demineralised water are added to the reaction apparatus (enamel apparatus). 50 kg of pasta seca are sieved into an intermediate tank via an Alexander sieve.

418 kg of methyl acetate are transferred into the reaction apparatus, and the sieved pasta seca is then added slowly with stirring.

The reaction mixture is then extracted for about 45 minutes at an internal temperature of 45° C., and transferred (nitrogen) into a centrifuge, and the raffinate is removed by centrifugation at 300 rpm. The residue is then spun dry at 500–800 rpm (Diolen spin dryer cloth). The raffinate, replenished with fresh pasta seca, can be employed for further extractions.

The extract is then mixed with 200 kg of water, and the methyl acetate is distilled off under atmospheric pressure at a maximum bottom temperature of 65° C. The distillate still contains about 5% by weight of water (by the Karl Fischer method) and can be re-used after adjustment of the water content. About 85% by weight of the methyl acetate employed are recovered in this way.

The aqueous distillation residue is cooled to 10° C. over the course of 2 hours, during which. the isoquercetin begins to precipitate. About 80% of the total amount of isoquercetin precipitating precipitates in very finely crystalline form with high purity (HPLC: about 94% of isoquercetin, 1% of rutin, 0.2% of quercetin) immediately during the cooling. The product must be separated off immediately (centrifuge), since on further stirring the crystal structure becomes coarser and the content drops since essentially only quercetin precipitates.

The filter cake is washed with water and spun dry.

The product is dried at a maximum drying temperature of 45° C. and at a pressure in the vacuum cabinet of about 100 mbar±20 mbar. 3.49 kg of dry product are obtained in this way.

EXAMPLE 2

In this example, the semi-continuous process on a laboratory scale is described:

Starting material: 500 g of mother-liquor residues (pasta), 8370 g of methyl acetate, demineralised water.

The methyl acetate (≅9000 ml) is combined with 1000 g of demineralised water in a stock tank to give the extractant. 2 litres of this solvent mixture are introduced into the extractor and heated to 45° C.

500 g of mother-liquor residues are stirred into the extractor. The extract is removed by suction through the sieve plate at a volume flow rate of 4 l/h and fed back into the extractor for 30 minutes.

After 30 minutes, the extract is fed continuously to a distillation apparatus; the loss of extractant is compensated by continuous supply of the remainder of the temperature-controlled extractant, so that the 2 l working volume in the extractor remains constant.

After the initially introduced extractant has been consumed after about 2 hours, the residue which remains is sucked dry.

All the methyl acetate is removed from the extract by distillation under atmospheric pressure during the extraction. The distillate still contains 4.2% of water (by the Karl Fischer method) and can be re-employed as extractant after adjustment of the water content.

The aqueous extraction residue which remains is allowed to cool to room temperature with stirring, sucked dry and rinsed with a little extractant. The crude isoquercetin solids= 135.4 g are obtained, HPLC: isoquercetin: 70%, rutin 25%, quercetin: 1%, remainder: 4%.

100 g of the crude isoquercetin are suspended in 1000 g of demineralised water and kept at the boil for 1 minute and immediately filtered off. In this way, pure isoquercetin (HPLC: 90%) is obtained in an amount of 44 g.

Isoquercetin crystallises out of the extract and can be re-employed in the purification together with crude isoquercetin.

What is claimed is:

1. A process for recovering isoquercetin from a bioflavanoid paste comprising
   a) extracting flavonoid from a bioflavonoid with a solvent mixture comprising methyl acetate: water in a volume ratio of 9:1, wherein the solvent mixture is present in a ten-fold excess, in comparison to the bioflavanoid paste based on weight, wherein the extraction is performed at a temperature of from 35° to 50° C., for at least 30 minutes, followed by separating isoguercetin from the resultant solid raffinate by centrifugation, b) diluting the resultant extract with water, c) removing methyl acetate from the extract by distillation under atmospheric pressure, d) cooling the resultant residue from the distillation to 10° C., whereby isoquercetin to precipitates, and e) separating and drying the resultant product.

2. A process according to claim 1, wherein the bioflavanoid paste, is obtained from a process wherein rutin was prepared from Dimorphandra gardneriana.

3. A process according to claim 1, wherein the solvent mixture is buffered with $NH_4HCO_3$.

4. A process according to claim 1, wherein the extraction is performed for 30 to 60 minutes.

5. A process according to claim 1, wherein the extract is diluted with about 60–80% by volume of water, based on the amount of extract.

6. A process according to claim 1, wherein diluting the extract and removing methyl acetate from the extract, or part thereof, are performed simultaneously.

7. A process according to claim 1, wherein the cooling of the residue takes place within 2 hours.

8. A process for recovering isoguercetin from a biofavanoid paste comprising passing a solvent mixture comprising methyl acetate: water in a volume ratio of 9:1 through an extractor that has a filter plate, wherein the extractor contains a suspension containing bioflavanoid paste, wherein the extractor volume and the volume flow rate or rates are set in such a way that a residence time in the extractor is at least 30 minutes, and wherein the temperature in the extractor is 35° to 50° C., followed by concentrating an extract that is withdrawn to form an aqueous residue.

9. A process according to claim 8, further comprising crystallizing or further purifying by boiling with water or by stirring with methyl tert-butyl ether the resultant product, wherein the crystallization or purification are being carried out in the extractor after withdrawal of the extract that forms the aqueous residue.

10. A process according to claim 1, wherein the solvent mixture is buffered.

11. A process according to claim 1, wherein the methyl acetate is acid-free methylacetate.

12. A process according to claim 1, wherein the water is demineralized water.

* * * * *

UNITED STATES PATENT AND TRADEMARK OFFICE
CERTIFICATE OF CORRECTION

PATENT NO. : 6,683,164 B1
DATED : January 27, 2004
INVENTOR(S) : Buchholz et al.

It is certified that error appears in the above-identified patent and that said Letters Patent is hereby corrected as shown below:

Column 5,
Line 5, change "isoguercetin" to -- isoquercetin --
Line 11, delete "to"

Column 6,
Line 3, change "isoguercetin" to -- isoquercetin --
Line 22, change "methylacetate" to -- methyl acetate --

Signed and Sealed this

Fourth Day of January, 2005

JON W. DUDAS
*Director of the United States Patent and Trademark Office*